United States Patent [19]

Ranken et al.

[11] Patent Number: 4,515,945

[45] Date of Patent: May 7, 1985

[54] N-ALKYL-4-(4-PYRIDINYL)ISATOIC ANHYDRIDES

[75] Inventors: Paul F. Ranken; Thomas J. Walter, both of Baton Rouge, La.

[73] Assignee: Ethyl Corporation, Richmond, Va.

[21] Appl. No.: 522,792

[22] Filed: Aug. 15, 1983

[51] Int. Cl.³ .................. C07D 265/26; C07D 215/16
[52] U.S. Cl. ..................................... 544/94; 546/156
[58] Field of Search ........................ 546/156; 544/94

[56] References Cited

U.S. PATENT DOCUMENTS

| | | | |
|---|---|---|---|
| 1,567,731 | 12/1925 | Günther | 544/94 |
| 3,753,933 | 8/1973 | Lesher | 260/286 |
| 3,838,156 | 9/1974 | Brundage | 544/94 |
| 3,907,808 | 9/1975 | Lesher | 260/287 R |
| 4,118,557 | 10/1978 | Lesher | 542/420 |

OTHER PUBLICATIONS

Mitscher et al., J. Med. Chem. 1978, vol. 21, No. 5, pp. 485-489.
Hardtmann et al., J. Hetercyclic Chem., vol. 12, 1975, pp. 565-572.

*Primary Examiner*—Paul M. Coughlan, Jr.
*Assistant Examiner*—Cecilia Shen
*Attorney, Agent, or Firm*—Donald L. Johnson; John F. Sieberth; Patricia J. Hogan

[57] ABSTRACT

N-alkyl-4-(4-pyridinyl)isatoic anhydrides are prepared by alkylating a 4-(4-pyridinyl)isatoic anhydride, suitably in the presence of sodium hydride and N,N-dimethylformamide. The products are particularly useful in the preparation of antibacterial 1-alkyl-1,4-dihydro-4-oxo-7-pyridinyl-3-quinolinecarboxylic acids.

3 Claims, No Drawings

N-ALKYL-4-(4-PYRIDINYL)ISATOIC ANHYDRIDES

FIELD OF THE INVENTION

This invention relates to N-alkyl-4-(4-pyridinyl)isatoic anhydrides, a process for preparing them, and processes for preparing derivatives thereof.

BACKGROUND

As disclosed in Sterling Drug's U.S. Pat. No. 3,753,993 (Lesher et al.), 3,907,808 (Lesher and Carabateas), and 4,118,557 (Lesher), it is known that antibacterial 1-alkyl-1,4-dihydro-4-oxo-7-pyridinyl-3-quinolinecarboxylic acids can be prepared from 4-(3-aminophenyl)pyridine. It is also known that this route to the bactericides, as disclosed, is less economical than might be desired.

From Mitscher et al., "Quinoline Antimicrobial Agents. 1. Versatile New Synthesis of 1-Alkyl-1,3-dihydro-4-oxo-3-quinolinecarboxylic Acids," *Journal of Medicinal Chemistry*, 1978, Vol. 21, No. 5, pp. 485-489, it is also known that antimicrobial agents related to the aforementioned bactericides can be prepared from the appropriate isatoic anhydrides.

It would be desirable to be able to prepare the antibacterial agents of Lesher, Lesher et al, and Lesher and Carabateas by a route similar to that employed by Mitscher et al; and 4-(4-alkyl-3-nitrophenyl)pyridines, as well as 2-nitro- and 2-amino-4-(4-pyridinyl)benzoic acids and 4-(4-pyridinyl)isatoic anhydrides, that are useful in this regard are disclosed in (1) copending application Ser. No. 511,887, filed July 8, 1983, in the name of Thomas J. Walter (Walter), (2) copending application Ser. No. 511,854, filed July 8, 1983, in the name of V. Ramachandran (Ramachandran), (3) copending application Ser. No. 511,844, filed July 8, 1983, in the name of Paul F. Ranken and Thomas J. Walter (Ranken and Walter), and (4) copending application Ser. No. 523,462, filed Aug. 15, 1983, in the names of Thomas J. Walter and Paul F. Ranken (Walter and Ranken).

From Hardtmann et al., *Journal of Heterocyclic Chemistry*, Vol. 12, p. 565 (1975), it is known that isatoic anhydride can be alkylated with a sodium hydride/ethyl bromide system to provide a 61% yield of N-ethyl isatoic anhydride after recrystallization.

SUMMARY OF INVENTION

An object of this invention is to provide N-alkyl-4-(4-pyridinyl)isatoic anhydrides which are convertible to 1-alkyl-1,4-dihydro-4-oxo-7-pyridinyl-3-quinolinecarboxylic acids.

Another object is to provide a process for preparing the N-alkyl-4-(4-pyridinyl)isatoic anhydrides.

A further object is to provide a process for preparing derivatives of the N-alkyl-4-(4-pyridinyl)isatoic anhydrides.

These and other objects are attained by alkylating a 4-(4-pyridinyl)isatoic anhydride to form an N-alkyl-4-(4-pyridinyl)-isatoic anhydride and, when appropriate, converting the anhydride to a desired derivative thereof.

DETAILED DESCRIPTION 4-(4-Pyridinyl)isatoic anhydrides utilizable in the practice of the invention are compounds corresponding to the formula:

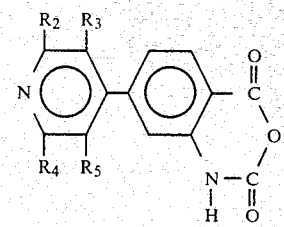

wherein $R_2$, $R_3$, $R_4$, and $R_5$ are independently selected from hydrogen and innocuous substituents, such as substituted (e.g., halogenated) and unsubstituted aryl or aryloxyaryl groups, halo, etc. These compounds can be prepared by the process of Walter and Ranken, the teachings of which are incorporated herein by reference—i.e., by reacting a 2-amino-4-(4-pyridinyl)benzoic acid with phosgene. As indicated in Walter and Ranken, the preferred 4-(4-pyridinyl)isatoic anhydride, when the aforementioned bactericides are to be prepared, is 4-(4-pyridinyl)isatoic anhydride itself.

In the process of the invention, the 4-(4-pyridinyl)isatoic anhydride is alkylated under conventional conditions, using a suitable alkylating agent, such as the alkyl halide appropriate for the particular N-alkyl compound to be prepared; a suitable base, such as sodium hydride; and a suitable medium, such as N,N-dimethylformamide or N,N-dimethylacetamide. A preferred alkylating agent when an unsubstituted N-alkyl group is desired is ethyl bromide. When an N-hydroxyalkyl or N-haloalkyl group is desired, it is generally preferred to use the appropriate vinyloxyalkyl halide to provide a vinyloxyalkyl compound, cleave it with aqueous acetic acid or the like to produce the hydroxyalkyl compound, and—when desired—halogenate the hydroxyalkyl compound with thionyl chloride or the like to produce a haloalkyl compound.

The amount of alkylating agent employed should be at least the stoichiometric amount, and optimum results are obtained when it is used in excess, e.g., about a 50% excess of the stoichiometric amount. Ordinarily, it is found preferable to vacuum-dry the 4-(4-pyridinyl)isatoic anhydride before combining it with the other ingredients to be employed in the reaction and to conduct the reaction in the presence of an excess of the base, e.g., about a 10% excess. Ambient temperatures are suitable for the reaction; and, as is customary for such reactions, the reaction is conducted in an inert atmosphere.

The N-alkyl-4-(4-pyridinyl)isatoic anhydrides formed in the process of the invention are novel compounds corresponding to the formula:

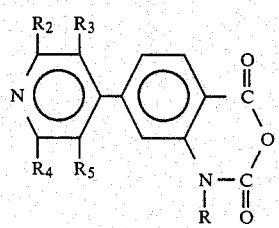

wherein R is the alkyl group contributed by the alkylating agent, generally an alkyl, haloalkyl, or hydroxyalkyl group containing 1-6 carbons, and $R_2$, $R_3$, $R_4$, and $R_5$ have the same definitions as given above. When the aforementioned bactericides are to be prepared, the preferred product is N-ethyl-4-(4-pyridinyl)-isatoic anhydride. These compounds are useful in the synthesis of a variety of materials but are particularly useful as intermediates in the production of the antibacterial 1-alkyl-1,4-dihydro-4-oxo-7-pyridinyl-3-quinolinecarboxylic acids of Lesher, Lesher et al., and Lesher and Carabateas, i.e., compounds corresponding to the formula:

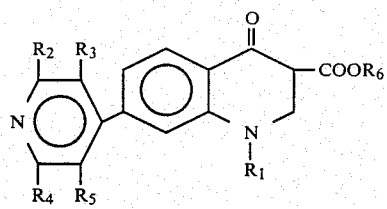

wherein $R_6$ is hydrogen or alkyl, $R_1$ is alkyl, haloalkyl, or hydroxyalkyl, and $R_2$, $R_3$, $R_4$, and $R_5$ have the same definitions as given above—any aliphatic groups generally containing 1–6 carbons.

The synthesis of these bactericides from the N-alkyl 4-(4-pyridinyl)isatoic anhydrides may be accomplished by:

(1) reacting the N-alkyl-4-(4-pyridinyl)isatoic anhydride with an alkali metal salt of an alkyl (e.g., ethyl) formyl acetate, as in Mitscher et al., to form an alkyl 1-alkyl-1,4-dihydro-4-oxo-7-pyridinyl-3-quinolinecarboxylate, e.g., ethyl 1-ethyl-1,4-dihydro-4-oxo-7-pyridinyl-3-quinolinecarboxylate, and (2) hydrolyzing the alkyl 1-alkyl-1,4-dihydro-4-oxo-7-pyridinyl-3-quinolinecarboxylate to the corresponding 1-alkyl-1,4-dihydro-4-oxo-7-pyridinyl-3-quinolinecarboxylic acid.

The following example is given to illustrate the invention and is not intended as a limitation thereof.

EXAMPLE

A slurry of 5.5 mmols of sodium hydride (99% pure) in 15 ml of N,N-dimethylformamide (DMF) was prepared in a dry box, and 5.5 mmols of neutralized, dried 4-(4-pyridinyl)isatoic anhydride were added thereto. The yellow slurry was stirred in a nitrogen atomosphere for 0.5 hour, after which 5.88 mmols of ethyl bromide were added. The reaction mixture was stirred overnight at room temperature, filtered, and distilled to remove the DMF. The yellow residue was slurried in methylene chloride, filtered, and dried to give a 71% yield of N-ethyl-4-(4-pyridinyl)isatoic anhydride as yellow crystals. Recrystallization from toluene provided the N-ethyl-4-(4-pyridinyl)isatoic anhydride as yellow needles having a melting point of 188°–190° C.

Yields varying from about 20% to about 90% were obtained by repeating the Example except for varying the amounts of the ingredients, the metalation and alkylation times, and/or the nature of the solvent employed.

It was found that the N-ethyl 4-(4-pyridinyl)isatoic anhydride prepared in the preceding examples cound be converted to 1-ethyl-1,4-dihydro-4-oxo-7-pyridinyl-3-quinolinecarboxylic acid by (a) reacting it with the potassium salt of ethyl formyl acetate to form ethyl 1-ethyl-1,4-dihydro-4-oxo-7-pyridinyl-3-quinolinecarboxylate, and (b) hydrolyzing that ester.

It is obvious that many variations may be made in the products and processes set forth above without departing from the spirit and scope of this invention.

We claim:

1. An N-alkyl-4-(4-pyridinyl)isatoic anhydride corresponding to the formula:

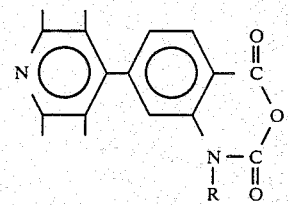

wherein R is an alkyl, haloalkyl, or hydroxyalkyl group containing 1–6 carbons.

2. The anhydride of claim 1 wherein R is alkyl.

3. The anhydride of claim 1 wherein R is ethyl.

* * * * *